United States Patent [19]

Yu et al.

[11] Patent Number: 5,641,475

[45] Date of Patent: *Jun. 24, 1997

[54] ANTIODOR, ANTIMICROBIAL AND PRESERVATIVE COMPOSITIONS AND METHODS OF USING SAME

[75] Inventors: Ruey J. Yu, Ambler; Eugene J. Van Scott, Abington, both of Pa.

[73] Assignee: TriStrata, Inc., Princeton, N.J.

[*] Notice: The term of this patent shall not extend beyond the expiration date of Pat. No. 5,258,391.

[21] Appl. No.: 333,159

[22] Filed: Nov. 1, 1994

Related U.S. Application Data

[60] Continuation-in-part of Ser. No. 276,275, Jul. 18, 1994, which is a division of Ser. No. 132,837, Oct. 7, 1993, abandoned, which is a division of Ser. No. 630,743, Dec. 20, 1990, Pat. No. 5,258,391, which is a continuation of Ser. No. 266,702, Nov. 3, 1988, abandoned, which is a continuation of Ser. No. 50,143, May 15, 1987, abandoned.

[51] Int. Cl.$^6$ .................................................... A61K 7/32
[52] U.S. Cl. .................... 424/65; 514/859; 514/863; 426/531; 426/652; 426/653; 426/654; 426/321; 426/323; 426/335; 252/397; 252/399; 252/404; 252/407
[58] Field of Search .................... 424/65; 514/859, 514/863; 426/531, 652, 653, 654, 321, 323, 335; 252/397, 399, 404, 407

[56] References Cited

U.S. PATENT DOCUMENTS

| | | | |
|---|---|---|---|
| 3,879,537 | 4/1975 | Van Scott et al. | 514/460 |
| 3,920,835 | 11/1975 | Van Scott et al. | 514/460 |
| 4,105,783 | 8/1978 | Yu et al. | 514/459 |
| 4,216,224 | 8/1980 | Yu et al. | 560/128 |
| 4,246,261 | 1/1981 | Van Scott et al. | 514/171 |
| 4,363,815 | 12/1982 | Yu et al. | 514/263 |
| 4,518,789 | 5/1985 | Yu et al. | 514/544 |
| 5,258,391 | 11/1993 | Van Scott et al. | 514/529 |

OTHER PUBLICATIONS

*Current Therapy*, p. 662 (1981).
*Current Therapy*, pp. 599–603 (1984).
*The Merck Index*, 9th Ed., Abstract 7961 (1976).

Primary Examiner—James J. Seidleck
Assistant Examiner—Michael A. Williamson
Attorney, Agent, or Firm—Panitch Schwarze Jacobs & Nadel, P.C.

[57] ABSTRACT

Therapeutic treatment as well as prophylactic measures are provided by topical application of compositions containing an aryl 2-acetoxyethanoic acid to eradicate or prevent the development of axillary foul odor, foot malodor and other body odors, e.g. scalp, and skin, nail and follicular infections caused by microorganisms. The compositions are antimicrobial against several organisms that infect the skin and are specifically effective against *P. acnes*. The compositions are therapeutically effective against folliculitis and perifolliculitis and are useful for other skin lesions, nail and mucosal infections such as impetigo, seborrheic dermatitis, erythrasma and trichomycosis axillaris, associated with or caused by microorganisms. The therapeutic effect of the composition may be synergized or amplified by incorporating a cosmetic or dermatologic agent into the formulation for topical treatment of cosmetic and dermatologic indications. The compositions are also useful as preservatives in food products, cosmetic and pharmaceutical formulations, and industrial preparations.

4 Claims, No Drawings

ANTIODOR, ANTIMICROBIAL AND PRESERVATIVE COMPOSITIONS AND METHODS OF USING SAME

CROSS-REFERENCE TO RELATED APPLICATIONS

This is a continuation-in-part of our copending application Ser. No. 08/276,275, filed Jul. 18, 1994 allowed Jan. 14, 1997, which is a division of application Ser. No. 08/132,837, filed Oct. 7, 1993, now abandoned, which is a division of application Ser. No. 07/630,743, filed Dec. 20, 1990, now U.S. Pat. No. 5,258,391, which is a continuation of application Ser. No. 07/266,702, filed Nov. 3, 1988, now abandoned, which is a continuation of application Ser. No. 07/050,143, filed May 15, 1987, now abandoned.

FIELD OF THE INVENTION

The invention relates to antiodor, antimicrobial and preservative compositions for prophylactic measures as well as topical treatment of skin foul odor and infections caused by microorganisms. More particularly, the invention is directed to compositions useful for topical application to treat and to prevent the development of axillary foul odor, foot malodor and other body foul odor, and to alleviate skin disorders associated with microbial infections, and also useful as preservatives in food products and cosmetic and pharmaceutical formulations.

BACKGROUND OF THE INVENTION

In human skin, sebaceous glands, eccrine sweat glands and apocrine glands secrete various chemicals onto the skin surface. These chemicals include sodium chloride, potassium bicarbonate, lactic acid, urea, squalene, proteins, carbohydrates, triglycerides and other lipids. Although body odor may be partially due to certain chemicals secreted by sebaceous glands and eccrine sweat glands, major axillary foul odor is due to secretions of the apocrine glands, which contain special nutrient materials for microorganisms.

Apocrine glands are located primarily in the axillae, anogenital region, mammary areolae, ear canals, eyelids, and are scattered on parts of the face, anterior chest and abdomen. In general, the apocrine duct opens into the upper end of the hair follicle although it may occasionally open directly onto the skin surface. In contrast to the eccrine glands, which produce a clear watery liquid, the apocrine glands secrete a milky fluid that has a pH range of 5 to 6.5 and initially consists of lipids, proteins and carbohydrates. Although fresh apocrine secretions do not have an objectionable odor, the secreted compounds are found to undergo decomposition by both chemical and microbial actions, and the degradation products are responsible for the offensive odors. Chemical substances identified as contributing to this unpleasant odor include lower organic acids such as butanoic, isopentanoic, hexanoic and octanoic acids; mercaptans; indoles; amines; hydrogen sulfide; ammonia; and phosphine. Although gram-positive bacteria, thriving on substances found on the moist skin surface, appear to be responsible for the production of malodor, the precise mechanisms of odor production are still unclear.

Most deodorant or antiperspirant products on the market today are salts of aluminum or zinc. The aluminum salts include aluminum chloride, aluminum chlorhydroxide, aluminum sulfate, aluminum potassium sulfate and aluminum phenolsulfonate. The zinc salts comprise zinc oxide, zinc peroxide, zinc stearate and zinc phenolsulfonate.

Although long-term use of aluminum or zinc salts as underarm deodorants presents no major problems in toxicity, those compounds do frequently cause irritation, burning, itching and other uncomfortable sensations to some people with sensitive skin. These people stop using underarm deodorants commonly available on the market today because of persistent itching or burning after use. Moreover, such irritation, burning and itching caused by underarm deodorants makes them even less suitable for application to other areas of the body which are even more sensitive than the underarm. Development of other efficacious anti-odorant substances which do not cause irritation or uncomfortable sensation when applied to the skin is therefore desirable.

Nail infections may be caused by gram-positive bacteria such as *Staphylococcus aureus* and *Streptococcus pyogenes*; gram-negative bacteria such as *Pseudomonas aeruginosa*; dermatophytes such as *Trichophyton rubrum* and *Trichophyton mentagrophytes*; yeasts such as *Candida albicans* or herpes simplex virus. In general, nail infections are difficult to treat by topical application, because most commercially available products are not formulated in bioavailable form to penetrate the hard nail plate.

Mucocutaneous integuments include for example oral mucosa, vaginal mucosa and anogenital areas. Although infections may be caused by bacteria, the most common forms are due to Candida yeasts and herpes virus. Vulvarvaginal infections may be caused for example by *Staphylococcus aureus, Pseudomonas aeruginosa, Candida albicans, Trichomonas vaginalis, Gardnerella vaginalis, Corynebacterium minutissimum* or herpes simplex Type I or Type II virus. The yeast infections are usually treated with butaconazole, clotrimazole, terconazole or miconazole cream for 3 to 7 days. The bacterial infections may be treated with oral administration of metronidazole 500 mg or clindamycin 300 mg twice daily for 7 days. For herpes infections, oral administration of acyclovir 200 mg 5 times daily for 10 days or topical application of 5% acyclovir ointment may be prescribed with various degrees of effectiveness.

Folliculitis and perifolliculitis are inflammatory disorders within or around the hair follicle, often caused by pathogenic bacteria or other microorganisms. The microorganisms may include *Staphylococcus aureus, Pseudomonas aeruginosa,* and *Propionibacterium acnes*. In most cases, scalp, face, chest, back and lower legs are involved. Folliculitis and perifolliculitis may be superficial infections and appear as small pustules in or around hair follicles. However, deeper infections may include lesions of papules and nodules. Patients may feel slight burning, itching and pain in the infected areas. Folliculitis may be persistent and last for months and even years. Topical application of mupirocin, chlorhexidine or aluminum chloride appears to be helpful and effective in many instances.

In our U.S. Pat. No. 4,363,815, entitled "Alpha Hydroxyacids, Alpha Ketoacids and Their Use in Treating Skin Conditions", we described and claimed that certain alpha hydroxyacids and related compounds are therapeutically effective for topical treatment of skin disorders associated with disturbed keratinization or inflammation. Such skin disorders include dry skin, ichthyosis, palmar and plantar hyperkeratosis, dandruff, Darier's disease, lichen simplex chronicus, keratoses, acne, psoriasis, eczema, pruritus and possibly warts and herpes. The alpha hydroxyacids and related compounds disclosed in the patent include phenyl 2-acetoxyethanoic acid (also known as phenyl alpha acetoxyacetic acid or O-acetylmandelic acid) which is a derivative compound formed by acetylation of the hydroxy group of mandelic acid.

In our U.S. Pat. No. 5,258,391, entitled "Phenyl Alpha Acyloxyalkanoic Acids, Derivatives and Their Therapeutic Use", we disclosed and claimed compositions containing these compounds for topical application to promote growth and hardening of nails and hair, wound healing and thickening of mucous membranes, skin and its appendages. However, compositions containing phenyl or diphenyl 2-acetoxyethanoic acid or their aryl or diaryl analogs have not previously been disclosed to be effective and useful for topical application to alleviate skin infections and body foul odor caused by one or more microorganisms.

BRIEF SUMMARY OF THE INVENTION

According to the present invention, it has been found that aryl or diaryl 2-acetoxyethanoic acids, when topically applied to body parts, such as the human axillae, foot or scalp, are useful in preventing and/or treating body foul odor. Further, according to the invention, it has been found that the topical application of aryl or diaryl 2-acetoxyethanoic acids to the skin, nails and mucosal membranes is therapeutically effective to eradicate or substantially improve skin lesions, such as folliculitis, perifolliculitis, impetigo, dandruff, seborrheic dermatitis, erythrasma and trichomycosis axillaris, and nail infections and mucosal infections, including oral infections and vaginal infections caused by various microorganisms. Further still, aryl or diaryl 2-acetoxyethanoic acids are useful as preservatives in food products, cosmetic and pharmaceutical formulations and industrial preparations.

The aryl or diaryl 2-acetoxyethanoic acids may be applied in various formulations such as solutions, gels, creams, lotions, stick, balm, sprays or powders in either anhydrous or aqueous vehicles. In addition, the compositions containing an aryl or diaryl 2-acetoxyethanoic acid may be formulated or applied contemporaneously with other topical agents to provide synergistic or amplified activity for cosmetic or dermatologic indications of the body part being treated.

DETAILED DESCRIPTION OF PREFERRED EMBODIMENTS

In accordance with the present invention aryl or diaryl 2-acetoxyethanoic acids which may be incorporated into topical compositions for body foul odor, skin, nail and mucosal infections and related dermatologic disorders or into food products, cosmetic or pharmaceutical formulations or industrial preparations as preservatives therefor, are shown by the following chemical structural formula

(I)

$$R_1R_2C(OCCH_3)COH$$

wherein $R_1$=an aryl group having 6 to 13 carbon atoms, and $R_2$=H or an aryl group having 6 to 13 carbon atoms. The hydrogen atoms of the aryl groups may be substituted by an element or group such as F, Cl, Br, I, OH, AcO (acetoxy) or a saturated or unsaturated radical having 1 to 9 carbon atoms, such as a lower alkyl or alkoxy.

Since $R_1$ and $R_2$ may both be aryl groups, the invention includes the use of both aryl and diaryl 2-acetoxyethanoic acids, but for ease of reference the compounds of formula (I) will be simply referred to herein as aryl 2-acetoxyethanoic acids. Aryl 2-acetoxyethanoic acids may also exist as stereoisomers such as D, L, and DL forms when $R_1$ and $R_2$ are not identical. Aryl 2-acetoxyethanoic acids may also be present as a free acid or a salt form with an inorganic or organic base.

Representative aryl 2-acetoxyethanoic acids include but are not limited to the following: phenyl 2-acetoxyethanoic acid, (wherein in formula I: $R_1=C_6H_5$, $R_2$=H); diphenyl 2-acetoxyethanoic acid, (wherein $R_1=C_6H_5$, $R_2=C_6H_5$); (4-methylphenyl) 2-acetoxyethanoic acid, (wherein $R_1=CH_3C_6H_4$, $R_2$=H); (4-hydroxyphenyl) 2-acetoxyethanoic acid, (wherein $R_1=HOC_6H_4$, $R_2$=H); (4-chlorophenyl) 2-acetoxyethanoic acid, (wherein $R_1=ClC_6H_4$, $R_2$=H); (2-chlorophenyl) 2-acetoxyethanoic acid, (wherein $R_1=ClC_6H_4$, $R_2$=H); (4-acetoxyphenyl) 2-acetoxyethanoic acid, (wherein $R_1=CH_3COOC_6H_4$, $R_2$=H); (4-chlorophenyl) (2-chlorophenyl) 2-acetoxyethanoic acid, (wherein $R_1=ClC_6H_4$, $R_2=ClC_6H_4$); (4-methylphenyl) (2-chlorophenyl) 2-acetoxyethanoic acid, (wherein $R_1=CH_3C_6H_4$, $R_2=ClC_6H_4$); and (2-Naphthyl) 2-acetoxyethanoic acid, (wherein $R_1=C_{10}H_7$, $R_2$=H). Preferred aryl and diaryl 2-acetoxyethanoic acids include but are not limited to the following: phenyl 2-acetoxyethanoic acid; diphenyl 2-acetoxyethanoic acid; (4-chlorophenyl) 2-acetoxyethanoic acid; (2-chlorophenyl) 2-acetoxyethanoic acid; and (4-chlorophenyl) (2-chlorophenyl) 2-acetoxyethanoic acid.

Skin infections are generally caused by microbial agents which include bacteria, yeasts, fungi and viruses. It now appears that the aryl 2-acetoxyethanoic acids may have cidal as well as static effects, i.e., killing as well as inhibiting the growth of microorganisms. These compounds can thus treat the infections as well as alleviating the symptoms thereof.

We have now discovered that aryl 2-acetoxyethanoic acids have unexpected, much broader therapeutic utility than previously described. Under standard microbial tests, this compound has been found to inhibit the growth of various bacteria including *Staphylococcus aureus*, *Staphylococcus epidermidis*, *Micrococcus sedentarius*, *Micrococcus luteus*, *Brevibacterium epidermis*, *Corynebacterium minutissium*, *Serratia marcescens*, *Pseudomonas aeruginosa*, *Escherichia coli*, and *Propionibacterium acnes*.

Aryl 2-acetoxyethanoic acid is specifically effective against the growth of *P. acnes* even in the presence of 10% lipid material in the test media. The inhibitory effect against *P. acnes* of this compound has been found to be greater than that of benzoyl peroxide under the same test conditions. Commonly used antiseptic compounds chlorhexidine gluconate and triclosan have been tested and compared under the same conditions and were found to be effective against various bacteria in the absence of lipid materials. However, chlorhexidine gluconate and triclosan have been found to be ineffective against most microorganisms when lipid materials are incorporated into the test media. In skin lesions, such as folliculitis, lipid materials including sebum secreted by sebaceous glands are present. In contrast to these two compounds, aryl 2-acetoxyethanoic acid has been found to be very effective against *P. acnes* even in the presence of lipid materials, particularly in treating and preventing the spread of acne vulgaris.

We have now discovered that a composition containing aryl 2-acetoxyethanoic acid is topically effective in preventing the development of, as well as in treating, body foul odor. Specifically, the composition is useful for topical application to prevent the development of axillary foul odor and foot malodor. The composition is also therapeutically effective for topical treatment of underarm foul odor and foot malodor.

We have also discovered that the compositions are useful for topical application to eradicate or substantially improve skin lesions such as folliculitis, perifolliculitis, impetigo, dandruff, seborrheic dermatitis, erythrasma and trichomycosis axillaris, and nail infections and mucosal infections including oral infections and vaginal infections caused by microbial organisms. These microorganisms include Staphylococcus species such as *S. aureus* and *S. epidermis;* Coryneform species such as Brevibacterium; *Propionibacterium acnes* such as *P. acnes, P. granulosum* and *P. avidum;* gram-negative bacteria including Proteus and *E. coli;* gram-positive bacillus and mycobacteria; and Pityrosporum species such as *P. ovale, P. orbiculae* and *Malassezia furfur.*

Aryl 2-acetoxyethanoic acids may also be incorporated into a food product or into a cosmetic or pharmaceutical composition as a preservative to prevent the growth of a microorganism.

We have further discovered that aryl 2-acetoxyethanoic acids can be synergistic to or can amplify the bioactivity of a dermatologic or topical agent. For example, salicylic acid may be useful as a keratolytic agent for topical treatment of follicular lesions associated with comedones or follicular occlusions. Salicylic acid, however, is not therapeutically effective against acne lesions associated with whiteheads caused by microbial infections including *P. acnes*. An amplifying composition containing salicylic acid and an effective amount of an aryl 2-acetoxyethanoic acid has been found to eradicate or substantially improve the clearing of both blackhead and whitehead lesions caused by physiologic factors and microbial infections.

We have further discovered that aryl 2-acetoxyethanoic acids can reverse a drug resistance to many dermatologic agents such as corticosteroids. For example, clobetasol propionate, betamethasone dipropionate, betamethasone valerate and triamcinolone acetonide are topically effective in the improvement of psoriatic lesions. Many patients however develop drug resistance to continued medications, a phenomenon known as tachyphylaxis or drug unresponsiveness. The cause for such drug unresponsiveness is unknown. It has been speculated that a receptor molecule for the corticosteroid might be depleted on chronic use of topical corticosteroid. At the time when the tachyphylaxis occurred on continued use of a corticosteroid, a composition containing an aryl 2-acetoxyethanoic acid was found to reverse such unresponsiveness, and psoriatic lesions began to improve.

Dermatologic agents and topical agents of cosmetic or pharmaceutical substances may be incorporated into the composition containing an aryl 2-acetoxyethanoic acid to amplify the bioactivity for topical treatment of various cosmetic and dermatologic indications. Topical agents which may be incorporated into the present composition include local analgesics and anesthetics, antiacne agents, antibacterial agents, antiyeast agents, antifungal agents, antiviral agents, antidermatitis agents, antipruritic (antiitch) agents, antiinflammatory agents, antiperspirants, antipsoriatic agents, antiaging and antiwrinkle agents, sunscreen and sunblock agents, skin lightening agents, depigmenting agents, vitamins, corticosteroids, hormones and retinoids. Examples of cosmetic and pharmaceutical agents include salicylic acid, pramoxine, clotrimazole, ketoconazole, miconazole, econazole, fluconazole, metronidazole, hydroxyzine, terbinafine, diphenhydramine, lidocaine, procaine, mepivacaine, monobenzone, erythromycin, tetracycline, clindamycin, meclocycline, hydroquinone, minocycline, naproxen, ibuprofen, theophylline, cromolyn, retinoic acid, 13-cis retinoic acid, hydrocortisone, hydrocortisone 21-acetate, hydrocortisone 17-valerate, hydrocortisone 17-butyrate, betamethasome valerate, betamethasone dipropionate, triamcinolone acetonide, fluocinonide, clobetasol, propionate, benzoyl peroxide, hydrogen peroxide, crotamiton, propranolol, promethazine, vitamin A palmitate, vitamin A acetate, and vitamin E acetate.

For example, treatment for nail infections may include compositions containing an aryl 2-acetoxyethanoic acid as the only active ingredient or compositions containing a dermatological or pharmaceutical agent and a synergistic amount of an aryl 2-acetoxyethanoic acid. The dermatological and pharmaceutical agents include, for example, clotrimazole, miconazole, econazole, ketoconazole, metronidazole, griseofulvin, ciclopirox, nystatin, polymyxin, dicloxacillin, fluconazole and acyclovir.

PREPARATION OF THERAPEUTIC/ PROPHYLACTIC COMPOSITIONS

Aryl 2-acetoxyethanoic acid compositions may be formulated in various forms, such as a solution, gel, cream, stick, balm, lotion, spray or powder form. In a typical anhydrous solution form, an aryl 2-acetoxyethanoic acid is dissolved in a mixture of ethanol and propylene glycol. The solution may contain the aryl 2-acetoxyethanoic acid in an amount from about 0.01% to about 99%, with a preferred concentration of about 0.05% to about 10%; ethanol in an amount from about 1% to about 90%, with a preferred concentration of about 20% to about 80%; and propylene glycol in an amount from about 1% to about 60%, with a preferred concentration of about 5% to about 40%. Unless otherwise indicated, all liquid percentages stated herein are weight/volume percent.

In the preparation of a composition in powder form, the aryl 2-acetoxyethanoic acid is first ground into fine powder with mortar and pestle or ball-mill machine, for example. The powdered substance is then mixed thoroughly with talc powder. The concentration of aryl 2-acetoxyethanoic acid may range from about 0.01% to about 20%, with a preferred concentration of about 0.02% to about 5%. Unless otherwise indicated, all solid percentages stated herein are percent by weight of total composition.

To formulate a synergistic or amplified composition an aryl 2-acetoxyethanoic acid may be directly incorporated into a composition containing a topical agent for cosmetic or dermatologic indications. Aqueous formulations are also possible by dissolving the aryl 2-acetoxyethanoic acid in ethanol, for example, then mixing with water. Propylene glycol and other common solvents may be added to such alcoholic aqueous solutions. Alternatively, the topical agent may be applied separately, but substantially contemporaneously, with the aryl 2-acetoxyethanoic acid.

The invention will now be described in more detail With reference to the following specific, non-limiting examples.

EXAMPLE 1

The following strains of microorganisms were used in Minimum inhibitory Concentration (MIC) tests for phenyl 2-acetoxyethanoic acid in this example and for benzoyl peroxide, chlorhexidine gluconate and triclosan in the following examples. In total, five strains were used for *S. aureus*, five strains were used for *S. epidermidis*, two strains were used for *M. sedentarius*, three strains were used for *M. luteus*, two strains were used for *B. epidermis*, three strains were used for *C. minutissium*, one strain was used for *S. marcescens*, three strains were used for *P. aeruginosa*, four strains were used for *E. coli*, and thirty-two strains were used for *P. acnes*.

Antimicrobial effects were determined based on MIC Agar Dilution Test utilizing Trypticase Soy Agar II (BBL) incorporation plates with and without 10% intralipid (Kabi Pharmacia Inc.). Initially, phenyl 2-acetoxyethanoic acid was prepared as a 2 mg/ml (0.2%) solution in water. This solution with serial dilution was incorporated into the test agar plates. The MIC test gave similar results when the same species but a different strain was used.

|    |                          | MIC (µg/ml) |       |
|----|--------------------------|-------------|-------|
|    |                          | No Lipid    | Lipid |
| 1. | Staphylococcus aureus    | 500         | 500   |
| 2. | Staphylococcus epidermidis | 1000      | 1000  |
| 3. | Micrococcus sedentarius  | 500         | 500   |
| 4. | Micrococcus luteus       | 1000        | 1000  |
| 5. | Brevibacterium epidermis | 1000        | 1000  |
| 6. | Corynebacterium minutissium | 500      | 500   |
| 7. | Serratia marcescens      | 1000        | 1000  |
| 8. | Pseudomonas aeruginosa   | 1000        | 1000  |
| 9. | Escherichia coli         | 1000        | 1000  |
| 10.| Propionibacterium acnes  | 250         | 250   |

The above results show that phenyl 2-acetoxyethanoic acid had inhibitory effects against all of the above bacteria, and the compound at 250 µg/ml (0.025%) concentration was specifically effective against the growth of *P. acnes* even in the presence of 10% lipid materials.

EXAMPLE 2 (COMPARATIVE)

Under the same test conditions described in Example 1, benzoyl peroxide was prepared as a 2.5 mg/ml (0.25%) solution in water. This solution with serial dilution was incorporated into the test agar plates. Typical test results are shown as follows.

|    |                          | MIC (µg/ml) |       |
|----|--------------------------|-------------|-------|
|    |                          | No Lipid    | Lipid |
| 1. | Staphylococcus aureus    | 2500        | 1250  |
| 2. | Staphylococcus epidermidis | 2500      | 1250  |
| 3. | Micrococcus sedentarius  | 2500        | 650   |
| 4. | Micrococcus luteus       | 2500        | 650   |
| 5. | Brevibacterium epidermis | 2500        | 1250  |
| 6. | Corynebacterium minutissium | 2500     | 1250  |
| 7. | Serratia marcescens      | 72500       | 1250  |
| 8. | Pseudomonas aeruginosa   | 72500       | 1250  |
| 9. | Escherichia coli         | 2500        | 1250  |
| 10.| Propionibacterium acnes  | 2500        | 625   |

The above results show that benzoyl peroxide was moderately effective against the growth of the above bacteria excluding *S. marcescens* and *P. aeruginosa* when lipid materials were present in the test medium.

EXAMPLE 3 (COMPARATIVE)

Under the same test conditions described in Example 1, chlorhexidine gluconate was prepared as a 2 mg/ml (0.2%) solution in water. This solution with serial dilution was incorporated into the test agar plates. Typical test results are shown as follows.

|    |                          | MIC (µg/ml) |       |
|----|--------------------------|-------------|-------|
|    |                          | No Lipid    | Lipid |
| 1. | Staphylococcus aureus    | 125         | >2000 |
| 2. | Staphylococcus epidermidis | 125       | >2000 |
| 3. | Micrococcus sedentarius  | 125         | >2000 |
| 4. | Micrococcus luteus       | 125         | >2000 |
| 5. | Brevibacterium epidermis | 250         | >2000 |
| 6. | Corynebacterium minutissium | 125      | >2000 |
| 7. | Serratia marcescens      | 1000        | >2000 |

-continued

|    |                          | MIC (µg/ml) |       |
|----|--------------------------|-------------|-------|
|    |                          | No Lipid    | Lipid |
| 8. | Pseudomonas aeruginosa   | 1000        | >2000 |
| 9. | Escherichia coli         | 250         | >2000 |
| 10.| Propionibacterium acnes  | 62.5        | >2000 |

The above results show that chlorhexidine gluconate was effective against the growth of the above bacteria when no lipid materials were present in the test medium. However, chlorhexidine gluconate was totally ineffective against the growth of the above bacteria when 10% lipid materials were incorporated in the test medium.

EXAMPLE 4 (COMPARATIVE)

Under the same test conditions described in Example 1, triclosan was prepared as a 10 mg/ml (1%) solution in water. This solution with serial dilution was incorporated into the test agar plates. Typical test results are shown as follows.

|    |                          | MIC (µg/ml) |        |
|----|--------------------------|-------------|--------|
|    |                          | No Lipid    | Lipid  |
| 1. | Staphylococcus aureus    | 156         | >10000 |
| 2. | Staphylococcus epidermidis | 156       | 5000   |
| 3. | Micrococcus sedentarius  | 156         | >10000 |
| 4. | Micrococcus luteus       | 156         | >10000 |
| 5. | Brevibacterium epidermis | 156         | >10000 |
| 6. | Corynebacterium minutissium | 156      | >10000 |
| 7. | Serratia marcescens      | >10000      | >10000 |
| 8. | Pseudomonas aeruginosa   | >10000      | >10000 |
| 9. | Escherichia coli         | 156         | >10000 |
| 10.| Propionibacterium acnes  | 156         | >10000 |

The above results show that triclosan was effective against the growth of the above bacteria excluding *S. marcescens* and *P. aeruginosa* in the absence of lipid materials. However, triclosan was ineffective against the growth of the above bacteria when 10% lipid materials were incorporated in the test medium.

EXAMPLE 5

A typical test for prophylactic effect in preventing the development of axillary foul odor was carried out as follows. A test composition was prepared by dissolving 0.5 g of phenyl 2-acetoxyethanoic acid or diphenyl 2-acetoxyethanoic acid in 70 ml of ethanol and 30 ml of propylene glycol. The control vehicle was prepared by mixing 70 ml of ethanol and 30 ml of propylene glycol. A human subject, male, age 71, was instructed to take a shower in the morning using ordinary soap to clean the body surfaces. After the skin was dried, the test composition was topically applied to the left underarm area only. The vehicle control was topically applied to the right underarm area. Both underarm areas were monitored by the subject and at least one other person approximately every 8 hours to determine whether the test composition had any prophylactic effect in preventing the development of underarm foul odor in the left axilla as compared to the vehicle alone on the right control armpit.

Presence or substantial absence of foul odor, detected by smell, was adopted as the criteria for ineffectiveness or effectiveness of the test composition. It was found that while the right control side developed foul odor within hours, the left underarm did not produce any detectable odor, even after 24 hours. This shows that the test composition containing 0.5% phenyl 2-acetoxyethanoic acid or diphenyl 2-acetoxyethanoic acid was substantially effective in preventing the development of axillary foul odor.

EXAMPLE 6

A typical test for axillary antiodor effectiveness was carried out as follows. A human subject, female, age 62, could not use existing commercial products of antiperspirants or deodorants because of severe itching and irritation after topical application. After the foul odor developed in both axillae, the subject was instructed to apply the same test composition as Example 5 containing 0.5% phenyl 2-acetoxyethanoic acid or diphenyl 2-acetoxyethanoic acid on the left side underarm and the control vehicle on the right side. Topical applications were made once daily for several days.

While the right armpit continued to produce foul odor, the left underarm ceased emanating any detectable foul odor after 1 day. The subject was instructed at this time to apply the test composition on the right side also. The right axilla ceased to emanate any detectable foul odor after 1 day of use. This shows that the test composition containing phenyl 2-acetoxyethanoic acid or diphenyl 2-acetoxyethanoic acid was topically effective in eradicating the axillary foul odor.

EXAMPLE 7

A typical test for prophylactic effect in preventing the development of, as well as treatment of, foot malodor was carried out as follows. A test composition in powder form was prepared by mixing 1 g of finely powdered phenyl 2-acetoxyethanoic acid with 99 g of talc powder. The talc powder alone was used as a control vehicle.

A human subject, female, age 23, had persistent foot malodor all year round. She had used commercially available foot products containing a mixture of undecylenic acid and zinc or calcium undecylenate with partial or little success in controlling the development of foot malodor. On the first morning, the subject was instructed to spread the test composition lightly on the left foot and also inside the hose. The control vehicle was used on the right foot and inside the hose. While the right foot developed malodor by the first evening, the left foot produced no detectable malodor. The subject was then instructed to apply the test composition on both feet the second morning. At the end of the second day, both feet produced no detectable malodor. The same topical applications were continued for several days; complete suppression of malodor was sustained. This shows that the test composition containing phenyl 2-acetoxyethanoic acid in powder form was topically effective in preventing the development of and in treating foot malodor.

EXAMPLE 8

A prophylactic and therapeutic composition containing an aryl 2-acetoxyethanoic acid and salicylic acid for topical treatment of skin infections may be formulated as follows. Phenyl 2-acetoxyethanoic acid 1.0 g and salicylic acid 2.0 g were dissolved in a mixture consisting of ethanol 70 ml, propylene glycol 26 ml and nonoxynol-6 1.0 ml. The solution thus obtained had pH 2.9. The composition thus formulated containing phenyl 2-acetoxyethanoic acid 1% and salicylic acid 2% is suitable for topical treatment of infected skin lesions including papular and pustular acne lesions.

EXAMPLE 9

A prophylactic and therapeutic composition containing an aryl 2-acetoxyethanoic acid and chlorhexidine for topical treatment of skin infections and body odors may be formulated as follows. Phenyl 2-acetoxyethanoic acid 0.3 g and chlorhexidine 0.1 g were dissolved in a mixture consisting of ethanol 70 ml, propylene glycol 28.6 ml and nonoxynol-9 1.0 ml. The solution thus obtained had pH 4.6. The composition thus formulated containing phenyl 2-acetoxyethanoic acid 0.3% and chlorhexidine 0.1% is suitable for topical treatment of body odors as well as skin infections including papular and pustular acne lesions.

EXAMPLE 10

A prophylactic and therapeutic composition containing an aryl 2-acetoxyethanoic acid and three other topical agents for topical treatment of skin infections may be formulated as follows. Phenyl 2-acetoxyethanoic acid 0.9 g, salicylic acid 2.0 g, tartaric acid 0.9 g and citric acid 0.9 g were dissolved in a mixture consisting of ethanol 70 ml, propylene glycol 24.4 ml and nonoxynol-11 0.9 ml. The solution thus obtained had pH 2.1. The composition thus formulated containing phenyl 2-acetoxyethanoic acid 0.9%, salicylic acid 2%, tartaric acid 0.9% and citric acid 0.9% is suitable for topical treatment of skin infections including papular and pustular acne lesions.

EXAMPLE 11

A prophylactic and therapeutic composition containing an aryl 2-acetoxyethanoic acid and other topical agents for topical treatment of skin infections may be formulated as follows. Phenyl 2-acetoxyethanoic acid or diphenyl 2-acetoxyethanoic acid 0.9 g., salicylic acid 2.0 g, tartaric acid 0.9 g, citric acid 0.9 g, retinyl acetate 0.9 g, triethyl citrate 20 g and BET 0.2 g were dissolved in a mixture consisting of ethanol 63.3 ml, propylene glycol 10 ml, and nonoxynol-11 0.9 ml. The composition thus formulated containing aryl 2-acetoxyethanoic acid 0.9%, salicylic acid 2%, tartaric acid 0.9%, citric acid 0.9%, retinyl acetate 0.9% and triethyl citrate 20% is suitable for topical treatment of skin infections including papular and pustular acne lesions.

EXAMPLE 12

A topical composition containing 3% aryl 2-acetoxyethanoic acid as the only active ingredient for treatment of nail infections may be formulated as follows: phenyl 2-acetoxyethanoic acid or diphenyl 2-acetoxyethanoic acid 3 g was dissolved in isopropyl alcohol 77 ml, butane-1,3-diol 15 ml and nonoxynol-6 5 ml. A synergistic composition may be formulated as follows: phenyl 2-acetoxyethanoic acid or diphenyl 2-acetoxyethanoic acid 1 g and clotrimazole 1 g were dissolved in ethanol 78 ml and propylene glycol 20 ml.

The participating subjects in the present study were instructed to apply twice daily the composition containing phenyl 2-acetoxyethanoic acid or diphenyl 2-acetoxyethanoic acid with or without clotrimazole as an additional antimicrobial agent. Nail infections usually disappeared within one to several months of topical application with the non-synergistic composition. The synergistic composition appeared to shorten the period of topical application and speed-up the healing of diseased nails.

EXAMPLE 13

Compositions for treatment of oral infections may contain an aryl 2-acetoxyethanoic acid as the only active ingredient. In this case a phenyl 2-acetoxyethanoic acid or diphenyl 2-acetoxyethanoic acid 2% composition was formulated by dissolving the active ingredient 2 g in ethanol 78 ml and propylene glycol 20 ml. Before use, this composition was diluted to 0.1% with water by mixing one part of the composition with 19 parts of water. The treatment involves oral rinse, wash and gargle by keeping the diluted composition inside the oral cavity for a few minutes, and then spit out. Such procedure may be repeated twice daily for several days until the infection is eradicated usually within 5–7 days.

A synergistic composition may be formulated by dissolving phenyl 2-acetoxyethanoic acid or diphenyl 2-acetoxyethanoic acid 1 g and a pharmaceutical agent such as ketoconazole or acyclovir 2 g in ethanol 77 ml and propylene glycol 20 ml. Before use, this composition was mixed with 19 parts of water. Oral treatment was carried out in the same procedure as the above.

EXAMPLE 14

Compositions for topical treatment of vulvar-vaginal infections may contain an aryl 2-acetoxyethanoic acid as the only active ingredient. In this case, phenyl 2-acetoxyethanoic acid or diphenyl 2-acetoxyethanoic acid 0.3 g was dissolved in ethanol 1 ml. The solution thus obtained was mixed with petrolatum 66 g and mineral oil 32.7 g. The ointment thus prepared may be applied topically twice daily to the affected areas for a few days to a few weeks.

A synergistic composition may be formulated by dissolving phenyl 2-acetoxyethanoic acid or diphenyl 2-acetoxyethanoic acid 0.1 g and clotrimazole 0.2 g in ethanol 2 ml and nonoxynol-6 5 ml. The mixture thus obtained was mixed with petrolatum 66 g and mineral oil 26.7 g. The topical formulation thus prepared may be applied twice daily to the affected area until the infection has subsided.

EXAMPLE 15

An aryl 2-acetoxyethanoic acid may be incorporated in food products, cosmetic and pharmaceutical formulations and industrial preparations as a preservative to prevent the growth of microorganism(s). The concentration of an aryl 2-acetoxyethanoic acid used may range from 0.01% to 1% with a preferred concentration of 0.02% to 0.2%.

An aryl 2-acetoxyethanoic acid may also be used in compositions as a routine oral hygiene aid. The concentration of the active ingredient may range from 0.01% to 0.5% with preferred concentration of 0.02% to 0.1%. An aryl 2-acetoxyethanoic acid may also be incorporated into soaps, soap bars, sticks, balms and the like for personal care and routine hygiene care. The concentrations may range from 0.01% to 1% with preferred concentration of 0.02% to 0.5%.

TEST RESULTS OVERVIEW

In order to determine the antimicrobial effect of an aryl 2-acetoxyethanoic acid, a standard test method of Minimum Inhibitory Concentration (MIC) against the growth of 10 bacteria was used. To determine a prophylactic effect against the development of, as well as a topical effect in the treatment of, body foul door, eleven human subjects participated in this study. More than twenty human subjects participated in a study to determine whether the compositions containing an aryl 2-acetoxyethanoic acid were therapeutically effective for topical treatment of folliculitis and other skin lesions, nail infections and mucosal infections caused by microbial infections. Scientific and test results are overviewed as follows.

I. Antimicrobial Test

Ten different species of bacteria were used in Minimum Inhibitory Concentration (MIC) tests. The bacteria include *S. aureus, S. epidermidis, M. sedentarius, M. luteus, B. epidermis, C. minutissium, S. marcescens, P. aeruginosa, E. coli,* and *P. acnes*. In addition various sources and strains of these bacteria were also included in the tests, and up to 32 different strains of *P. acnes* were used.

The test substance selected from phenyl 2-acetoxyethanoic acid, benzoyl peroxide, chlorhexidine gluconate and triclosan was dissolved in water, and the solution with serial dilution was incorporated into the test agar plates. The plates containing different concentrations of test substance were inoculated with a strain of bacterium. MIC is defined as the lowest concentration of the test substance in the plate in which there is no growth of the microorganism.

Phenyl 2-acetoxyethanoic acid showed inhibitory effects against the growth of all ten bacteria tested, with or without the presence of 10% lipid materials. The compound of the present invention was specifically effective against *P. acnes* at 0.025% concentration even in the presence of lipid materials.

In some instances, different strains of one bacterium might have given rise to slightly different inhibitory effects. In general, however, different sources or strains of the same species were found to give basically very similar results. For example, five strains of *S. epidermis* from 5 sources with numbers Atcc 35984, Atcc 31432, Atcc 14490, Dh 557 and Dh 640 gave identical results. Thirty-two different strains of *P. acnes* (twenty from acne lesions and the remaining twelve from other sources) all gave identical results.

Under the same test conditions, benzoyl peroxide at 0.0625% concentration showed inhibitory effects against *M. sedentarius, M. lutens,* and *P. acnes* in the presence of 10% lipid materials. This antiacne compound was not effective against the growth of all the bacteria tested in the absence of lipid materials.

Chlorhexidine gluconate at 0.02 to 0.05% concentration is used as a general antiseptic on skin and mucous membranes. Under the same test conditions chlorhexidine gluconate at 0.006 to 0.1% concentration was found to be effective against all the bacteria tested in the absence of lipid materials. However, this antiseptic substance was not effective against the growth of all the bacteria tested in the presence of lipid materials.

Triclosan at 1% concentration is used in liquid and bar soap as a disinfectant and medicated cleanser for acne-prone skin. Under the same test conditions triclosan at 0.0156% concentration was found to be effective against all the bacteria except *S. marcescens* and *P. aeruginosa* in the absence of lipid materials. However, this disinfectant was not effective against the growth of all the bacteria tested in the presence of 10% lipid materials.

The above antimicrobial test results show that the phenyl 2-acetoxyethanoic acid is the most active and effective compound against *P. acnes* with or without the presence of lipid materials in the test medium.

II. Body Odor

A. Axillary Foul Odor

A total of seven subjects (four females ages 62, 64, 78, and 81; three males ages 36, 38 and 68) participated in several studies. Most of these subjects could not use existing commercial products of antiperspirants or deodorants because of severe irritation after topical application. Phenyl 2-acetoxyethanoic acid or diphenyl 2-acetoxyethanoic acid 0.5% concentration and a control vehicle (70 volume % ethanol, 30 volume % propylene glycol) were prepared in one-ounce container bottles according to the examples. The participating subjects were instructed to take a shower in the morning using ordinary soap to clean the body surfaces. After the skin was dried, the test composition containing 0.5% aryl 2-acetoxyethanoic acid was topically applied to the left underarm area only. The control vehicle was topically applied to the right underarm area. Topical applications were repeated 8 hours later.

Both underarm areas were monitored by the subject and at least one other person approximately every 8 hours to determine whether the test composition had any prophylactic effect in preventing the development of underarm foul odor in the left axilla as compared to the vehicle alone on the right control underarm. The criteria for ineffectiveness or effectiveness of the test composition were based on presence or absence of foul odor as detected by olfactory sense of smell. It was found in all the participating subjects that while the right control side developed underarm foul odor by 8 hours, the left axilla did not produce any detectable odor, even after 16 hours. This test result shows that the composition containing 0.5% aryl 2-acetoxyethanoic acid is topically effective in preventing the development of axillary foul odor.

The axillary antiodor effectiveness was determined as follows. The above participating subjects were instructed to topically apply the test composition containing 0.5% phenyl 2-acetoxyethanoic acid or diphenyl 2-acetoxyethanoic acid on the right underarm and discontinue the use of the control vehicle after the foul odor had developed. The subjects continued to use the same test composition containing 0.5% phenyl 2-acetoxyethanoic acid or diphenyl 2-acetoxyethanoic acid on the left underarm. Topical applications were repeated 8 hours later. Thereafter topical applications were made once daily for several days. In all the subjects tested the right axilla ceased to emanate any detectable foul odor after 2 to 3 days of topical use. The left axilla continued to maintain the condition free of any offensive foul odor.

In another study the subjects were instructed not to take a shower in the morning. After the foul odor developed in both axillae, the subjects were instructed to apply the test composition containing 0.5% phenyl 2-acetoxyethanoic acid or diphenyl 2-acetoxyethanoic acid on the left underarm area and the control vehicle on the right underarm area. Topical applications were made once daily for several days.

While the right underarm continued to produce foul odor, the left underarm diminished in intensity of foul odor after one to two days of topical application. Usually the left underarm ceased emanating any detectable foul odor after 1 day of topical use. The subjects were instructed at this time to apply the test composition containing 0.5% phenyl 2-acetoxyethanoic acid or diphenyl 2-acetoxyethanoic acid on the right underarm area also. Topical applications were made once daily for several days. The right axilla ceased to emanate any detectable foul odor after 1 to 2 days of topical use.

The above results show that the composition containing 0.5% aryl 2-acetoxyethanoic acid is topically effective in preventing the development of axillary offensive odor and is also therapeutically effective for topical treatment of underarm foul odor.

B. Foot Malodor

A total of six subjects (three females ages 23, 35, and 57; three males ages 43, 61 and 70) participated in several studies. Most of these participants had used commercially available products for foot malodor including those containing a mixture of undecylenic acid and zinc or calcium undecylenate without much success in controlling the development of foot malodor.

A test composition containing 1% phenyl 2-acetoxyethanoic acid in powder form was prepared by mixing thoroughly 1 g of finely powdered compound with 99 g of talc powder. The talc powder alone was used as a control vehicle. The test composition and the control vehicle were packaged in one-ounce powder containers. The participating subjects were instructed to lightly spread the test composition on the bottom of the left foot and inside the hose or sock on the first morning.

The criteria for ineffectiveness or effectiveness of the test composition were based on presence or absence of malodor as detected by olfactory sense of smell. Both feet were monitored by the subject and at least one other person in the evening. While the right foot developed malodor by the first evening, the left foot produced no detectable malodor in all the participating subjects.

The subjects were then instructed to apply the test composition on both feet the next morning. At the end of the second day, both feet produced no detectable malodor. The same topical applications were continued by all the participants for several days to confirm the above results.

The test results show that the test composition containing 1% phenyl 2-acetoxyethanoic acid was topically effective in preventing the development of and was also therapeutically effective for topical treatment of foot malodor.

III. Folliculitis and Perifolliculitis

Nine patients having various degrees of folliculitis and perifolliculitis participated in this study. A test composition containing 0.9% phenyl 2-acetoxyethanoic acid or diphenyl 2-acetoxyethanoic acid was prepared by dissolving 0.9 g compound in 79.1 ml 2-propanol, 15 ml butane-1,3-diol and 5 ml nonoxynol-6. The composition was packaged in one-ounce bottles. The patients were instructed to apply the test composition twice daily on the infected skin lesions and involved areas. Topical applications were continued up to 8 weeks. The results showed that skin lesions of superficial folliculitis and perifolliculitis were eradicated or substantially improved after a few days of topical applications. Deeper lesions of papules were found to be eradicated or substantially improved after 4 to 8 weeks of topical applications.

IV. Therapeutic Response and Amplified Effects (a) Acne

Twelve patients having moderate to severe acne lesions consisting of pustules and papules participated in this study. The test composition containing 2% salicylic acid and 1% phenyl 2-acetoxyethanoic acid or diphenyl 2-acetoxyethanoic acid was prepared by dissolving 2 g salicylic acid and 1 g aryl 2-acetoxyethanoic acid in 70 ml ethanol, 26 ml propylene glycol and 1 ml nonoxynol-6 or 1 ml nonoxynol-11.

The patients were instructed to topically apply the test composition twice daily on the affected areas of the skin for 4 to 8 weeks. Acne lesions were recorded at the beginning and at the end of 4 weeks and 8 weeks of topical applications. Ten of twelve patients showed substantial reduction in the number of pustular and papular lesions after 4 to 8 weeks of topical treatment with the test composition containing both salicylic acid and phenyl or diphenyl 2-acetoxyethanoic acid. On continued use of the test composition new lesions of pustules and papules did not appear over the next 8 weeks. This indicated that the test composition has a prophylactic effect in preventing the development of new acne lesions.

(b) Psoriasis

Psoriasis is not an infection disease but rather a disorder caused by genetic factors and is a chronic skin disease affecting approximately 1 to 3% of the population. This disease is characterized by silver scales and thick, dry, red skin. Although corticosteroids such as clobetasol propionate, betamethasone dipropionate, betamethasone valerate and triamcinolone acetonide are topically effective in the control of psoriatic lesions, many patients have developed resistance to continued medications.

To determine the therapeutic responsive effect of an aryl 2-acetoxyethanoic acid against psoriasis seven patient participated in this study. A test composition was prepared by dissolving 1 g phenyl 2-acetoxyethanoic acid or diphenyl 2-acetoxyethanoic acid in 2 ml ethanol. The solution thus obtained was mixed with 60 g petrolatum and 37 g mineral oil. The anhydrous ointment thus formulated was packaged in one-ounce jars.

When the drug unresponsiveness to a corticosteroid occurred, the participating patients were instructed to apply in addition the test composition once daily to the lesions on the left side of the body only. Topical applications of the corticosteroid were continued twice daily to both sides of the body. Psoriatic lesions on the left side of the body began to improve after one week of additional topical application with the composition containing phenyl 2-acetoxyethanoic acid or diphenyl 2-acetoxyethanoic acid. While psoriatic lesions on the right side of the body remained unresponsive to the topical corticosteroid, the lesions on the left side started to clear after 3 to 4 weeks of additional topical application with the composition containing an aryl 2-acetoxyethanoic acid.

At this time the patients were instructed to shift the additional topical application to the lesions on the right side instead of the left side of the body. The psoriatic lesions on the right side of the body began to clear after 3 to 4 weeks of additional topical application with the composition containing aryl 2-acetoxyethanoic acid.

We have also found that the test composition containing aryl 2-acetoxyethanoic acid could be used in conjunction with a corticosteroid product at the beginning of topical treatment to prevent the development of tachyphylaxis to corticosteroid.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition for preventing and treating body foul odor, for treating infections of the skin, nails and mucosal membranes, and for preserving food products, cosmetic and pharmaceutical formulations, and industrial preparations, comprising a bioactive cosmetic, dermatologic or preservative agent and an amount of an aryl 2-acetoxyethanoic acid effective as a synergist or amplifier to enhance the bioactivity of said agent.

2. A composition according to claim 1, wherein the aryl 2-acetoxyethanoic acid has the chemical structural formula

wherein $R_1$=an aryl group having 6 to 13 carbon atoms, and $R_2$=H or an aryl group having 6 to 13 carbon atoms, said acid including stereoisomers thereof, and free acids or salt forms thereof with an organic or inorganic base.

3. A composition according to claim 1, wherein said aryl 2-acetoxyethanoic acid is phenyl 2-acetoxyethanoic acid.

4. A composition according to claim 1, wherein said aryl 2-acetoxyethanoic acid is diphenyl 2-acetoxyethanoic acid.

* * * * *